(12) United States Patent
Tegels

(10) Patent No.: US 9,955,958 B2
(45) Date of Patent: May 1, 2018

(54) EXTRA-VASCULAR CLOSURE DEVICE WITH RELEASABLE SEALING PLUG

(71) Applicant: ST. JUDE MEDICAL PUERTO RICO LLC, Caguas, PR (US)

(72) Inventor: Zachary J. Tegels, Minnepolis, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 195 days.

(21) Appl. No.: 13/760,966

(22) Filed: Feb. 6, 2013

(65) Prior Publication Data

US 2014/0222066 A1    Aug. 7, 2014

(51) Int. Cl.
*A61B 17/08*    (2006.01)
*A61B 17/00*    (2006.01)

(52) U.S. Cl.
CPC .... *A61B 17/0057* (2013.01); *A61B 17/00491* (2013.01); *A61B 2017/0065* (2013.01);
(Continued)

(58) Field of Classification Search
CPC .......... A61B 17/0057; A61B 17/12109; A61B 17/12136; A61B 2017/00526; A61B 2017/0065; A61B 2017/00654; A61B 2017/00623; A61B 17/00491; A61B 2017/00575; A61B 2017/00579; A61B 2017/00584; A61B 2017/00588; A61B 2017/00592; A61B 2017/00601; A61B 2017/00606; A61B 2017/0061; A61B 2017/00615; A61B 2017/00628; A61B 2017/00632; A61B 2017/00659; A61B 2017/12054; A61B 17/08; A61B 17/083; A61B 2017/00597; A61B 2017/00619; A61B 2017/00637; A61B 2017/00641; A61B 2017/00646; A61B 2017/00668; A61B 2017/00663; A61B 2017/00672;
(Continued)

(56) References Cited

U.S. PATENT DOCUMENTS 5,545,178 A * 8/1996 Kensey ............. A61B 17/0401
604/15
5,700,277 A * 12/1997 Nash ................. A61B 17/0057
128/887
(Continued)

FOREIGN PATENT DOCUMENTS

WO        0019912 A1    4/2000
WO   WO 2011/019374 A1 *  2/2011
WO     2012148745 A1    11/2012

OTHER PUBLICATIONS

PCT International Search Report for PCT Application No. PCT/US2013/069604, dated Jun. 2, 2014 (4 pp.).

*Primary Examiner* — Darwin Erezo
*Assistant Examiner* — Katherine Schwiker
(74) *Attorney, Agent, or Firm* — Dorsey & Whitney LLP

(57) ABSTRACT

A vascular closure device includes a handle, a carrier tube, a sealing tip, a sealing tip connection member, and an actuator. The carrier tube extends from the handle. The sealing tip is positioned at a distal end of the carrier tube. The sealing tip connection member extends from the sealing tip to the handle. The actuator is mounted to the handle and operable to move the sealing tip connection member to release the sealing tip from the carrier tube.

17 Claims, 14 Drawing Sheets

(52) U.S. Cl.
CPC ............... *A61B 2017/00477* (2013.01); *A61B 2017/00526* (2013.01); *A61B 2017/00557* (2013.01); *A61B 2017/00654* (2013.01); *Y10T 29/49826* (2015.01)

(58) Field of Classification Search
CPC .... A61B 2017/00676; A61B 2017/081; A61B 2017/088; A61B 2017/1205; A61B 2017/00004; A61M 25/04
USPC ......... 606/213–215, 217, 191–192, 194–195
See application file for complete search history.

(56) References Cited

U.S. PATENT DOCUMENTS

| | | | |
|---|---|---|---|
| 6,183,496 B1* | 2/2001 | Urbanski | A61B 17/0057 606/151 |
| 2005/0283187 A1* | 12/2005 | Longson | A61B 17/0057 606/213 |
| 2006/0135991 A1* | 6/2006 | Kawaura | A61B 17/0057 606/213 |
| 2006/0241579 A1* | 10/2006 | Kawaura | A61B 17/0057 606/39 |
| 2009/0171387 A1* | 7/2009 | Pipenhagen | A61B 17/0057 606/213 |
| 2009/0216267 A1* | 8/2009 | Willard | A61B 17/0057 606/213 |
| 2010/0211000 A1* | 8/2010 | Killion et al. | 604/57 |
| 2010/0217309 A1* | 8/2010 | Hansen | A61B 17/0057 606/213 |
| 2011/0166595 A1 | 7/2011 | Vidlund et al. | |
| 2011/0224719 A1* | 9/2011 | Fortson | 606/213 |
| 2012/0022562 A1* | 1/2012 | Willard | A61B 5/0086 606/151 |
| 2012/0109189 A1* | 5/2012 | Voss | A61B 17/0057 606/213 |
| 2012/0310275 A1* | 12/2012 | Zhou et al. | 606/213 |
| 2013/0190812 A1* | 7/2013 | Vidlund | A61B 17/0057 606/214 |

* cited by examiner

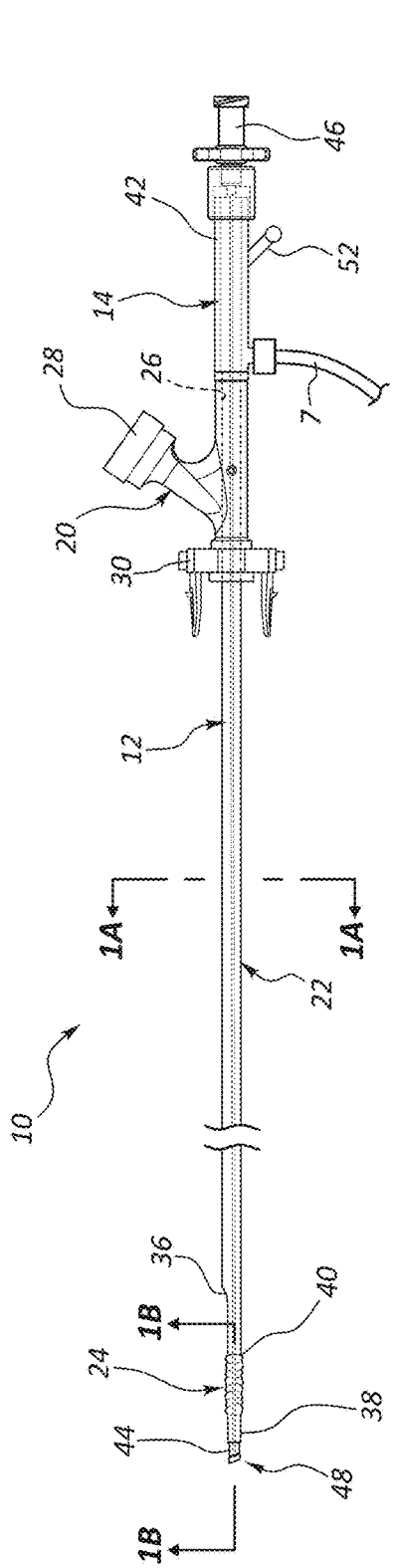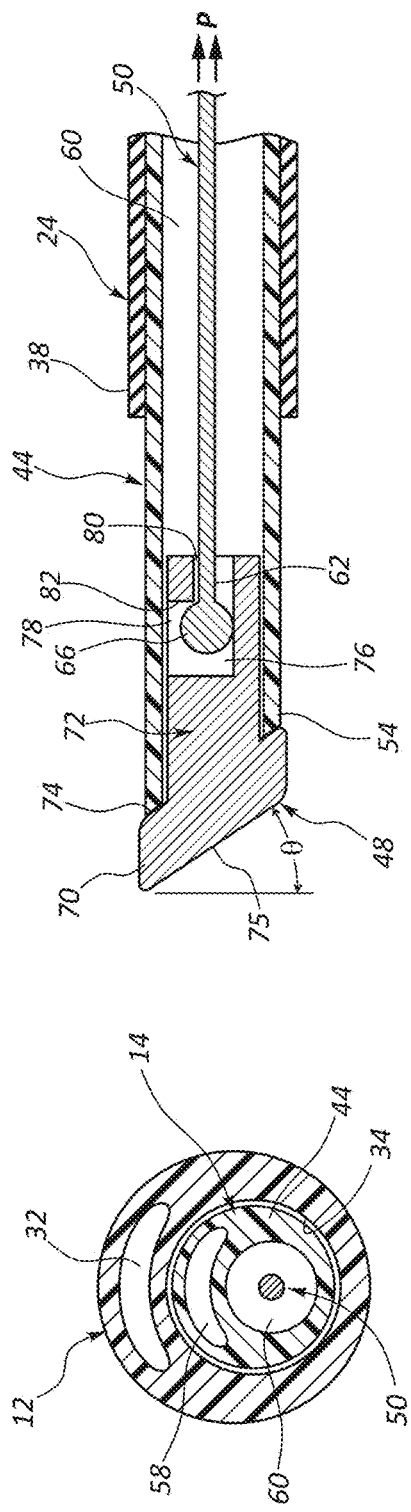

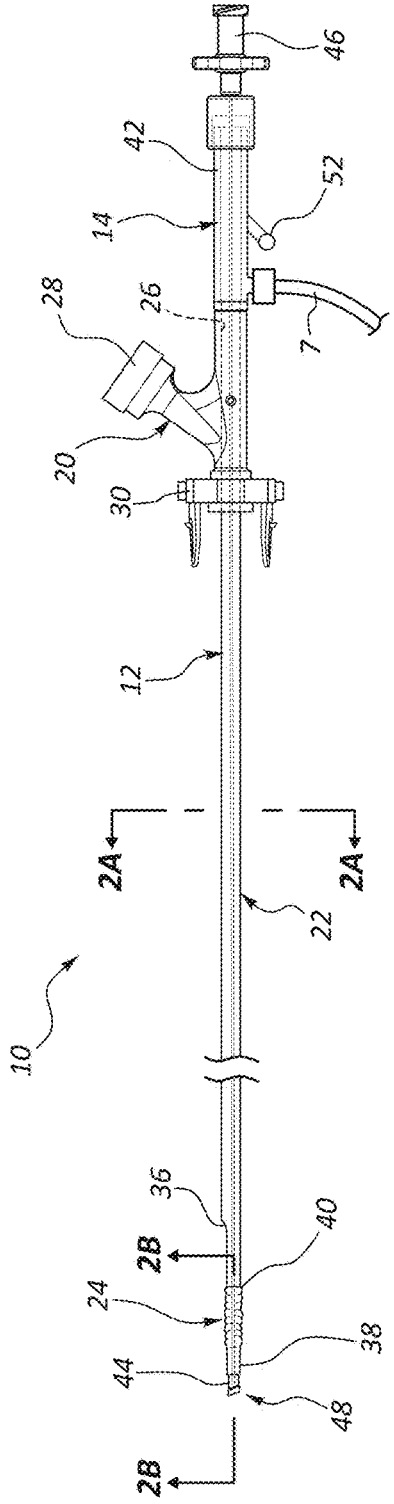
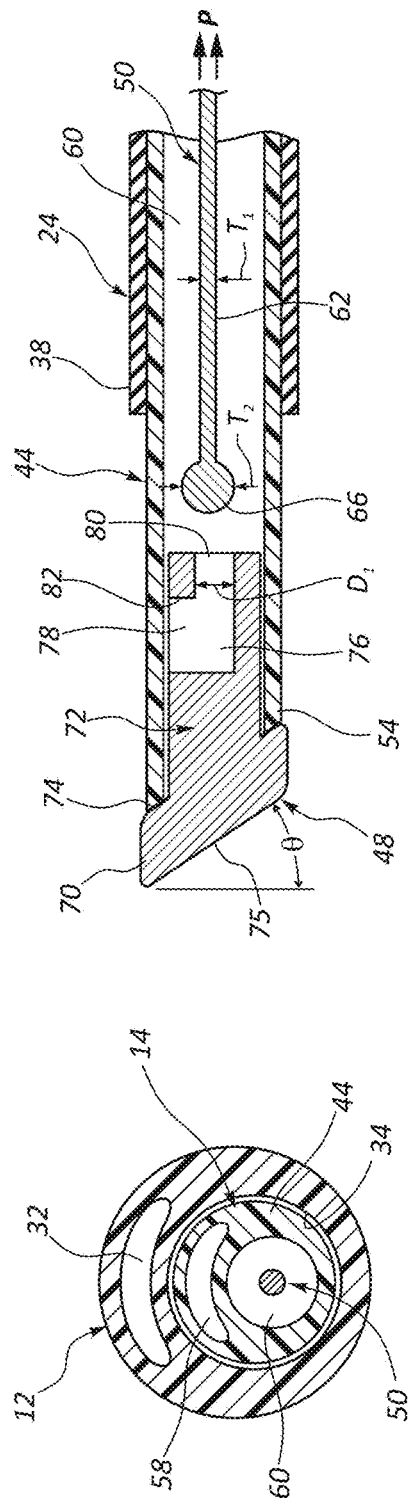
FIG. 2
FIG. 2A
FIG. 2B

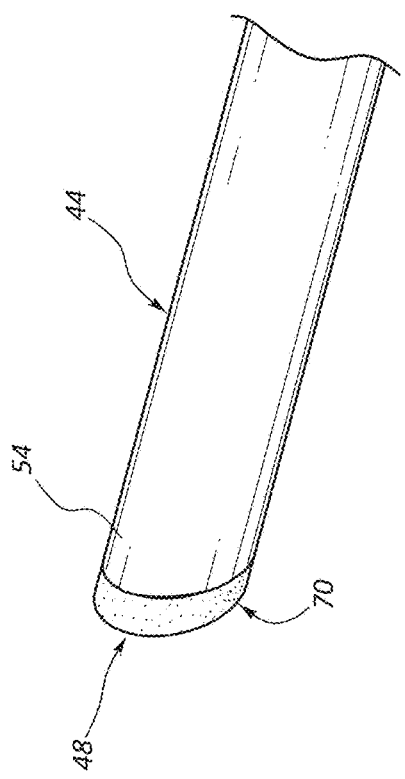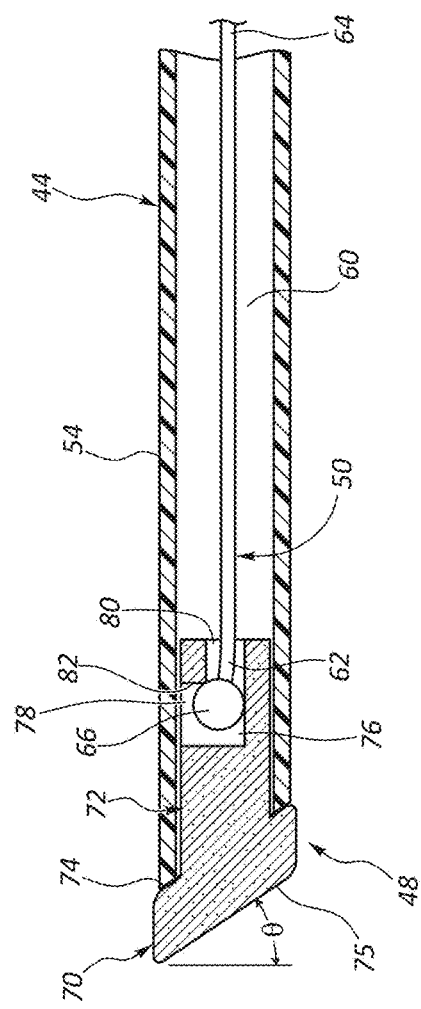

EXTRA-VASCULAR CLOSURE DEVICE
WITH RELEASABLE SEALING PLUG

TECHNICAL FIELD

The present disclosure relates generally to methods and systems for sealing tissue punctures, and more particularly, to methods and systems for depositing a sealing member to seal tissue punctures.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices.

While there are a variety of prior art devices and techniques for closing such punctures, one method includes temporarily sealing the vessel puncture intravascularly using an inflation balloon. A sealing material may be delivered to an outer surface of the vessel to seal the vessel puncture while the temporary seal from the balloon is maintained. Removing the collapsed balloon through the sealing material may leave a tract through the sealing material. Challenges exist in closing the tract to maintain hemostasis.

SUMMARY

One aspect of the present disclosure relates to a vascular closure device that includes a handle, a carrier tube, a sealing tip, a sealing tip connection member, and an actuator. The carrier tube extends from the handle. The sealing tip is positioned at a distal end of the carrier tube. The sealing tip connection member extends from the sealing tip to the handle. The actuator is mounted to the handle and operable to move the sealing tip connection member to release the sealing tip from the carrier tube.

The sealing tip connection member may include a wire having a retention member at a distal end thereof, and applying a tension force in the wire with the actuator disconnects the retention member from the sealing tip. The sealing tip may include a body portion and a head portion, wherein the body portion is positioned in the carrier tube and the head portion is positioned outside of the carrier tube. The head portion may include a distal end surface that is arranged at a non-perpendicular angle relative to a longitudinal dimension of the body portion. The carrier tube may include a lumen, and the sealing tip connection member extends through the lumen.

The vascular closure device may include a hypotube extending through the lumen, and the sealing tip connection member extends through the hypotube. The sealing tip may include a cavity sized to receive a connection portion of the sealing tip connection member, wherein the connection portion is releasable from the cavity upon operation of the actuator. The cavity may be accessible from a first opening in a sidewall of the sealing tip and a second opening in a distal end of the sealing tip, and the sealing tip connection member is insertable through the first opening and out of the second opening with the connection portion being retained in the cavity.

Another aspect of the present disclosure relates to a vascular closure device for sealing a vessel puncture of a patient. The vascular closure device includes a sealant delivery device, and a detachable sealing tip assembly. The sealant delivery device is configured to deposit a volume of flowable sealant adjacent to a vessel puncture. The detachable sealing tip assembly is configured to seal a channel formed in the flowable sealant upon removal of the vascular closure device from the patient. The detachable sealing tip assembly includes a carrier tube, a sealing tip positioned at a distal end of the carrier tube, and a filament having a distal end releasably connected to the sealing tip and a proximal end operable by an actuator to disconnect the sealing tip within the channel.

The sealant delivery device may include a lumen sized to receive the carrier tube. The sealing tip may include a proximal portion sized to extend into the carrier tube, and a distal portion positioned outside of the carrier tube. The filament may be connected to the sealing tip prior to inserting the sealing tip into the carrier tube. The filament may include one of a wire and a suture.

Another aspect of the present disclosure relates to a method of sealing a vessel puncture. The method includes providing a vascular closure device having a sealing tip, a sealing tip connection member, and an actuator, wherein the sealing tip connection member extends from the sealing tip to the actuator. The method also includes advancing the vascular closure device to the vessel puncture, delivering a volume of flowable sealant to the vessel puncture, withdrawing a portion of the vascular closure device through the flowable sealant to define a channel in the flowable sealant, positioning the sealing tip in the channel, and operating the actuator to release the sealing tip connection member from the sealing tip to seal the channel.

Operating the actuator to release the sealing tip connection member from the sealing tip may include removing a connection portion of the sealing tip connection member from within the sealing tip. The vascular closure device may include a carrier tube, wherein the sealing tip is releasably connected to a distal end of the carrier tube, and releasing the sealing tip connection member from the sealing tip disconnects the sealing tip from the carrier tube. Operating the actuator may apply tension in the sealing tip connection member. The method may include providing a sealant delivery device to deliver the volume of flowable sealant to the vessel puncture, wherein the vascular closure device extends through the sealant delivery device.

A further aspect of the present disclosure relates to a method of assembling a vascular closure device. The method includes providing a sealing tip, a sealing tip connection member, an actuator, a handle, a carrier tube, and a sealant delivery device, the sealing tip having a cavity with first and second access openings, the sealing tip connection member having a connection portion at a distal end thereof, and the actuator being mounted to the handle. The method includes inserting a proximal end portion of the sealing tip connection member into the cavity of the sealing tip through the first access opening and out of the cavity through the second access opening. The connection portion is releasably held in the cavity. The method also includes inserting a portion of the sealing tip into a distal open end of the carrier tube and connecting the proximal end portion of the sealing tip connection member to the actuator. The sealant delivery device is operable to deliver a volume of flowable sealant to a vessel puncture, and the actuator is operable to disconnect the sealing tip connection member from the sealing tip to deposit the sealing tip within the flowable sealant.

The first access opening may be formed in a sidewall of the sealing tip, the second access opening may be formed in a proximal end of the sealing tip, and the connection portion may have a minimum size that is greater than a maximum size of the second access opening.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

FIG. 1 is a side view of an example vascular closure device in accordance with the present disclosure.

FIG. 1A is a cross-sectional view of the vascular closure device of FIG. 1 taken along cross-section indicators 1A-1A.

FIG. 1B is a cross-sectional view of the vascular closure device of FIG. 1 taken along cross-section indicators 1B-1B.

FIG. 2 is a side view of the vascular closure device of FIG. 1 operated to release a sealing tip.

FIG. 2A is a cross-sectional view of the vascular closure device of FIG. 2 taken along cross-section indicators 2A-2A.

FIG. 2B is a cross-sectional view of the vascular closure device of FIG. 2 taken along cross-section indicators 2B-2B.

FIG. 11A is a perspective view of a portion of the vascular closure device of FIG. 1 in a third stage of assembly.

FIG. 11B is a cross-sectional view of the vascular closure device of FIG. 11A.

Throughout the drawings, identical reference numbers designate similar, but not necessarily identical, elements.

DETAILED DESCRIPTION

Figure 3:
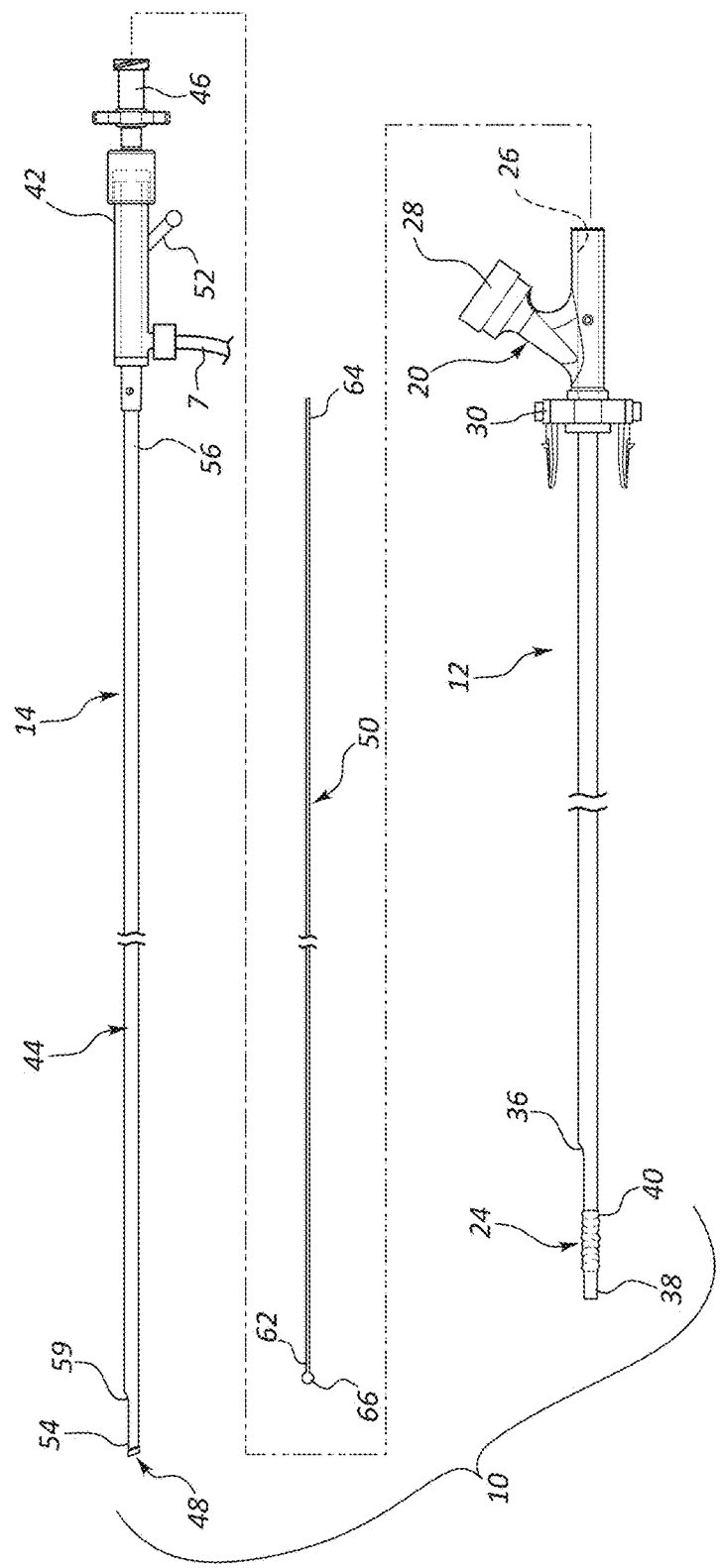
FIG. 3 is an exploded view of the vascular closure device of FIG. 1.

The systems disclosed herein may be used to close or seal percutaneous punctures made through the body tissue of a patient to gain access to a body cavity of a patient. Access through these percutaneous punctures allows a physician to carry out various procedures in or through the body cavity for examination, surgery, treatment and the like. While not meant to be limiting, the systems are illustrated being used to seal percutaneous punctures that provide access to blood vessels in patients for various procedures. It will be appreciated that the systems are applicable to other procedures requiring sealing of a puncture through body tissue into a cavity including, for example, laparoscopic surgery and other microscopic surgery techniques using a relatively small incision.

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

As used in this specification and the appended claims, the terms "engage" and "engageable" are used broadly to mean interlock, mesh, or contact between two structures or devices. Likewise "disengage" or "disengageable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as well as their derivatives, as used in the specification, including the claims, have the same meaning as the word "comprising."

An exemplary embodiment of the present disclosure includes a vascular closure device having a detachable sealing tip. The vascular closure device is used with a sheath that provides access through a vessel puncture and into an inner lumen of the vessel. The vascular closure device operates to release a detachable sealing plug (e.g., sealing tip) from a distal end of the vascular closure device after deployment of a flowable sealant at the vessel puncture. The vascular closure device may include a sealant delivery device and a locating device (also referred to as a temporary sealing device) such as a balloon location device. The locating device is inserted through the vessel puncture and anchors against an internal surface of the vessel adjacent to the vessel puncture. The sealant delivery device deposits a volume of flowable sealant along an external surface of the vessel adjacent to the vessel puncture. After the sealant is deposited, the location device is withdrawn through the sealant, which leaves an opening or channel through the center of the sealant. The channel may be sealed by locating and releasing the sealing tip, which is positioned on the distal end of the vascular closure device within the channel.

The sealing tip may be secured at the distal end of the location device using an elongated connection member such as, for example, a wire, suture or other linkage that extends along a length of the location device from the sealing tip at a distal end of a location device to a handle or housing at a proximal end of a location device. The sealing tip is released from the distal end of the location device by operating an actuation member such as a lever or other feature, which is located at the housing. Operating the actuation member moves the elongate connection member proximally, distally, or radially to release the sealing tip. In one example, a suture under tension retains the sealing tip at a distal end of the location device. The suture may be pulled proximally to release the sealing tip. Alternatively, the suture may be cut at the distal or proximal end of the location device. In another example, a wire having a connection portion at a distal end thereof is connected to the sealing tip with a snap-fit or press-fit connection. Applying a proximally directed tension force in the wire releases the connection so that the sealing tip may be deposited in the channel of the sealant.

The connection member (e.g., wire or suture), which secures the sealing plug (e.g., sealing tip) to the location device, may extend through an inflation lumen of the location device. In other examples, the connection member may extend through a tube or lumen that extends along a length of the location device from the housing to the distal tip. In other examples, a separate lumen is provided in the location device through which the connection member extends. The separate lumen may be radially spaced apart from an inflation lumen, which is used to deliver inflation fluid to an expandable anchor member (e.g., inflatable balloon).

In another arrangement, the sealant delivery device includes multiple lumens, wherein one lumen provides delivery of sealant to the vessel puncture and the other lumen provides a passage for advancing the location device to the vessel puncture. The lumen that receives the location device may provide delivery of inflation fluid to a balloon or other locating device that is positioned at a distal end portion of the location device or the sealant delivery device.

One aspect of the present disclosure relates to releasing the sealing tip within a channel of the deposited sealant without using the distal end of the delivery sheath or other device as a backstop to help locate and release the sealing tip. The step surface in the sealing tip in prior designs may define a catch point that inhibits precise placement of the sealing tip within the channel in the deposited sealant. The step surface in prior designs may also catch in a side branch vessel or plaque in the vessel prior to positioning the sealing tip within the channel of the deposited sealant. The sealing tip of the present disclosure may have a limited sized step feature that is operable by contact against a distal end surface of the location device rather than against a distal end surface of an insertion sheath. The sealing tip may be completely insertable within the insertion sheath. In some arrangements, the sealing tip may be operable without a step feature.

Another aspect of the present disclosure relates to the angled shape of a distal end portion of the sealing tip. The sealing tip may include a distal head portion having a distal surface that is arranged at an angle relative to a longitudinal axis of the sealing tip or a longitudinal axis of the location device. The distal surface may be arranged at an angle that substantially matches an angle of insertion of the vascular closure device through a percutaneous incision that provides access to the vessel puncture. The angle may be in the range of about 30° to about 60°, and more specifically may be in a range of about 30° to about 45°. The angle of the distal surface may be arranged non-perpendicular to a longitudinal dimension (e.g., longitudinal axis) of the sealing tip.

Referring now to FIGS. 1-3, an example vascular closure device 10 is shown including a sealant delivery device 12 and a balloon location device 14. The balloon location device 14 is inserted through a lumen of the sealant delivery device 12 to position a detachable sealing tip 48 distal of a distal opening 36 of a sealant delivery lumen of the sealant delivery device 12. The detachable sealing tip is positioned distal of a balloon 24 carried at least in part by one of the sealant delivery device 12 and balloon location device 14.

The sealant delivery device 12 includes a manifold 20, a delivery tube 22, and a balloon 24. The manifold 20 includes a delivery device passage 26, an injection port 28, and a connector 30. The delivery tube 22 includes a first lumen 32 and a second lumen 34. The first lumen 32 includes a distal opening 36. The balloon 24 includes distal and proximal waists 38, 40. A volume of sealant is delivered through the injection port 28 and into the first lumen 32, and is deposited adjacent to a vessel puncture upon ejection from the distal opening 36.

The distal and proximal waists 38, 40 of balloon 24 may be connected to a distal end portion of the delivery tube 22. In other arrangements, only the proximal waist 40 is connected to the distal end portion of the delivery tube 22, and the distal waist 38 is connected to a portion of the balloon location device 14. As mentioned above, the second lumen 34 may provide a path for inflation fluid to be delivered to the balloon 24. In other arrangements, the inflation fluid is delivered through the balloon location device 14.

The balloon location device 14 may include a housing or handle 42, a carrier tube 44, an inflation manifold 46, a detachable sealing tip 48, and a sealing tip connection member 50. The housing 42 is connected to a proximal end 56 of the carrier tube 44. In at least some arrangements, the distal waist 38 is connected to a distal end 54 of the carrier tube 44 (see FIG. 1B). The carrier tube 44 may include an inflation lumen 58 and a connector lumen 60. In other arrangements, the inflation lumen 58 and connector lumen 60 are integrated into a single lumen, such as when the second lumen 34 of sealant delivery device 12 provides delivery of inflation fluid to the balloon 24. The inflation lumen 58 may include a distal opening 59 that is in flow communication with the balloon 24. The distal opening 59 may be positioned proximal of the detachable sealing tip 48 (see FIG. 3).

The inflation manifold 46 may be connected to a source of inflation fluid 7. The inflation manifold 46 may be positioned at any desired location relative to the manifold 20 of sealant delivery device 12 and housing 42. Inflation manifold 46 is typically coupled in fluid communication with the inflation lumen 58.

The detachable sealing tip 48 may be mounted to the distal end 54 of carrier tube 44. The portion of the detachable sealing tip 48 may be inserted within the carrier tube 44 such as, for example, within the connector lumen 60 (see FIG. 1B).

The detachable sealing tip 48 may include a head portion 70, a body portion 72, and a face 75 (e.g., a step feature) defined between the head and body portions 70, 72. The head portion 70 may include a proximal stop surface 74. In other arrangements, the head portion 70 has the same peripheral size and shape as the body portion 72 so that there is no proximal stop surface 74.

Figure 4:
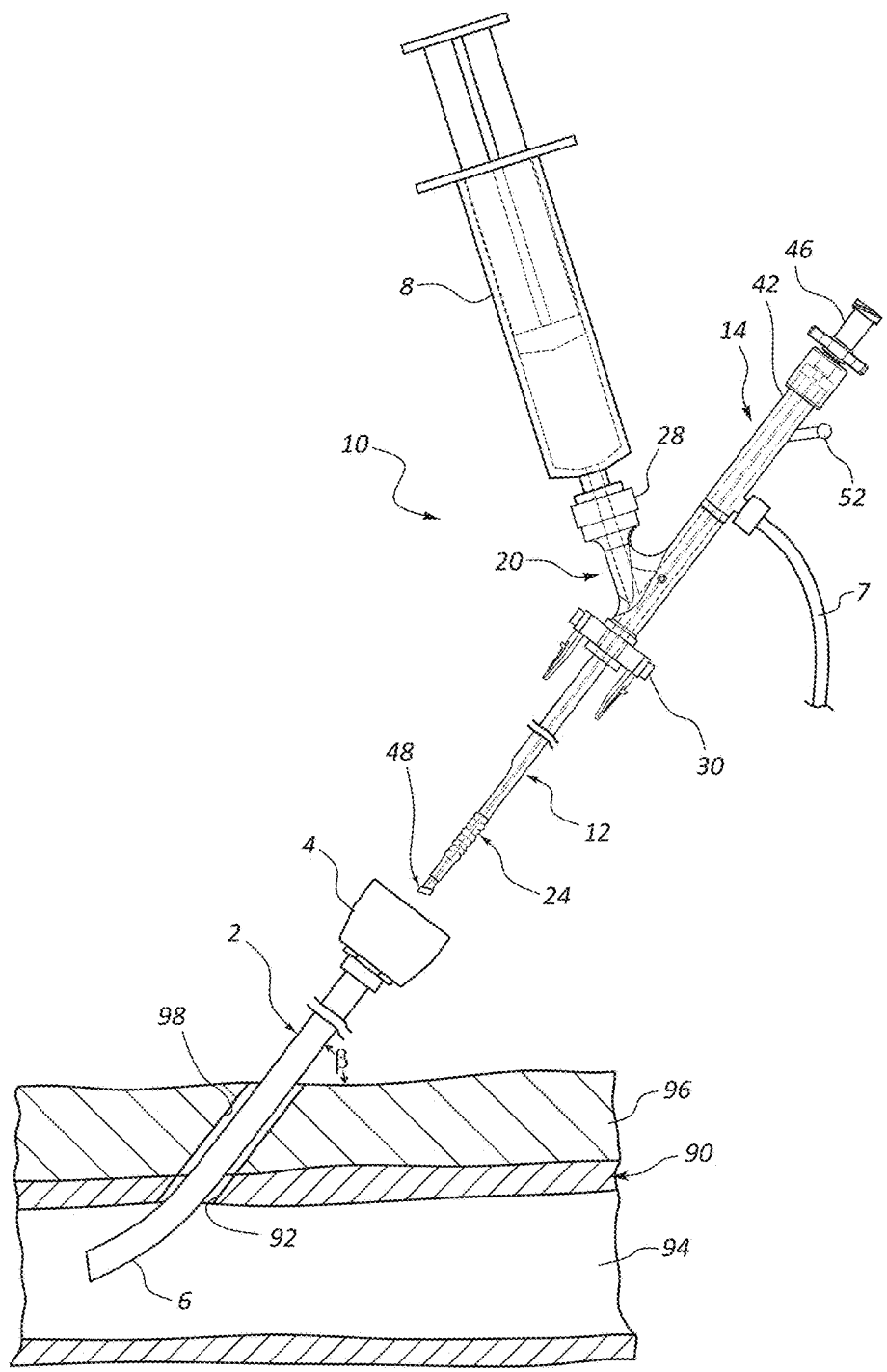
FIGS. 4-8 show steps of sealing a vessel puncture using the vascular closure device of FIG. 1.

The body portion 72 may include a cavity 76, a side opening 78, a proximal opening 80, and a stop surface 82 (see FIGS. 1B and 9A-11B). As clearly shown in FIGS. 1B, 2B, 8-10B, and 11B-14, the proximal stop surface 74 may be substantially planar. The cavity 76 is accessible through the side opening 78 and the proximal opening 80. The side opening 78 may have a greater size than the proximal opening 80. The face 75 may be arranged at an angle θ (see FIGS. 1B and 2B). The angle θ is typically about the same as the angle of insertion β of the vascular closure device 10 into a patient through a percutaneous incision as shown in FIG. 4. For example, the angle θ may be in the range of about 15° to about 45°, and more preferably about 30° to about 40°. The angle of face 75 may orient the face 75 flush against an outer surface of the vessel adjacent to the vessel puncture.

The sealing tip connection member 50 includes distal and proximal ends 62, 64, and a connection portion 66. The sealing tip connection member 50 may be an elongate member such as, for example, a wire, suture, braid, or filament. The connection portion 66 may have an enlarged size (e.g. maximum width or thickness dimension) as compared to the remaining portions of the sealing tip connection member 50. For example, the sealing tip connection member 50 may have a thickness $T_1$ in the range of about 0.5 mm to about 2 mm. A maximum dimension $T_2$ of the connection portion 66 may be in the range of about 2 mm to about 5 mm. In some arrangements, the dimension $T_2$ is at least two times greater than a dimension $T_1$ of the sealing tip connection member 50 (see FIG. 2B). The dimension $T_2$ is typically greater than a minimum dimension $D_1$ of the proximal opening 80. The connection portion 66 may contact the stop surface 82 adjacent to the proximal opening 80 to at least temporarily hold the connection portion 66 within the cavity 76 (see FIG. 1B).

Figure 9A:
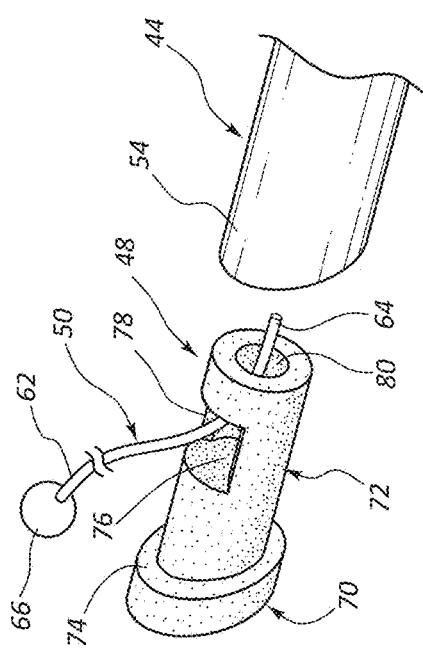
FIG. 9A is an exploded perspective view of a portion of the vascular closure device of FIG. 1 in a first state of assembly.
Figure 9B:
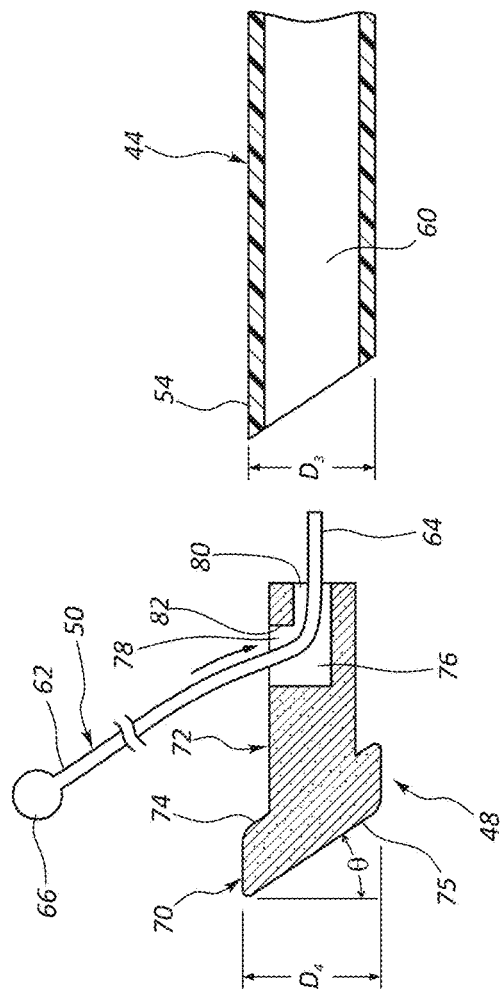
FIG. 9B is a cross-sectional view of the vascular closure device of FIG. 9A.
Figure 10A:
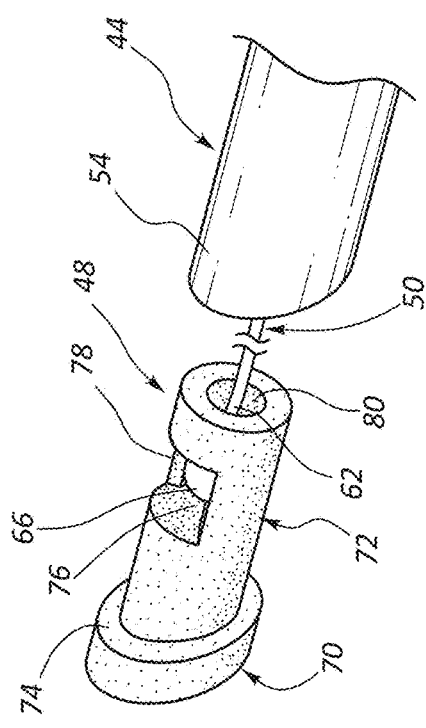
FIG. 10A is an exploded perspective view of the vascular closure device of FIG. 1 in a second stage of assembly.
Figure 10B:
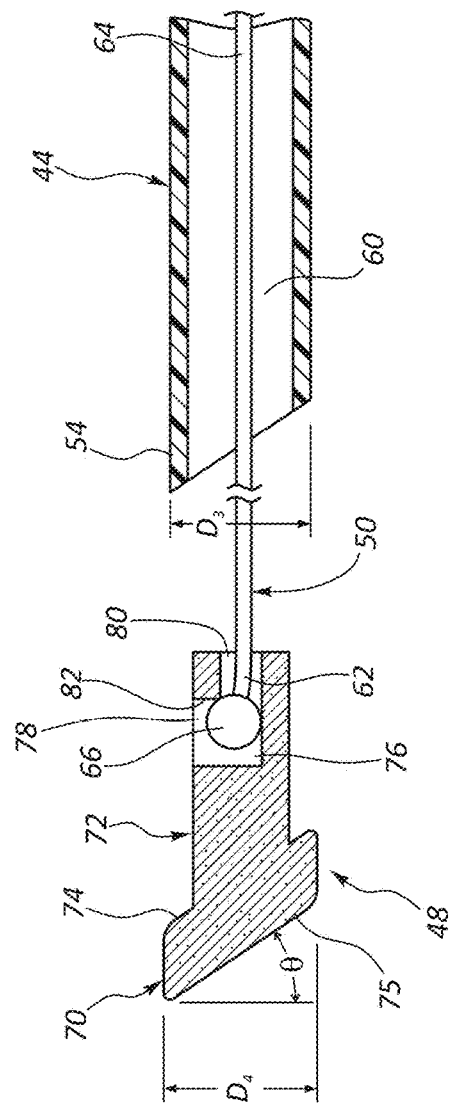
FIG. 10B is a cross-sectional view of the vascular closure device of FIG. 10A.

Referring to FIGS. 9A and 9B, the balloon location device 14 is assembled by inserting a proximal end 64 of the sealing tip connection member 50 through the side opening 78 into the cavity 76 and out through the proximal opening 80. The sealing tip connection member 50 is advanced through the cavity 76 until the connection portion 66 contacts the stop surface 82 as shown in FIGS. 10A and 10B. The proximal end 64 of the sealing tip connection member 50 is advanced through the connector lumen 60 of the carrier tube 44 and connected to the actuator 52. The body portion 72 of the detachable sealing tip 48 is inserted into the connector lumen 60 until the proximal stop surface 74 of the head portion 70 contacts a distal end surface of the carrier tube 44 as shown in FIGS. 11A and 11B.

The sealing tip connection member 50 is detached from the detachable sealing tip 48 to release the detachable sealing tip 48 from the vascular closure device 10. Operating the actuator 52 from a first position shown in FIG. 1 to a second or actuated position as shown in FIG. 2 may apply a tension force in the sealing tip connection member 50 that pulls the connection portion 66 through the proximal opening 80, thereby releasing the detachable sealing tip 48. The detachable sealing tip 48 may be released from the vascular closure device 10 without using an insertion sheath (e.g., delivery sheath 2 shown in FIGS. 4-8) as a backstop. In other arrangements, the balloon location device 14 includes a separate tube (e.g. stainless hypotube or polymer tube) or other backstop feature positioned within the connector lumen 60. The sealing tip connection member 50 may extend through the separate tube or backstop feature. The separate tube or backstop feature may support the detachable sealing tip 48 while applying the tension force in sealing tip connection member 50 to remove the connection portion 66 through the proximal opening 80. In this arrangement, the head portion 70 may be void of the proximal stop surface 74 and may be position at least partially within the carrier tube 44.

In other arrangements, the connection portion 66 is detachable from the sealing tip connection member 50 to provide release of the detachable sealing tip 48 from the vascular closure device 10. The connection portion 66 may provide a releasable connection such as, for example, a snap-fit, press-fit, or interference fit connection with the detachable sealing tip 48. The connection portion 66 may be replaced with other connection features to provide a temporary connection of the sealing tip connection member 50 to the detachable sealing tip 48.

As mentioned above, the sealing tip connection member 50 may be detachable from the detachable sealing tip 48 using other operations such as, for example, advancing or rotating the sealing tip connection member 50 relative to the detachable sealing tip 48. Alternatively, the sealing tip connection member 50 may be severed or cut at a location near the distal end of the balloon location device 14, or at a proximal end near the housing 42. This severing or cutting of the sealing tip connection member 50 may provide a temporary disconnection of the detachable sealing tip 48 from the balloon location device 14. The sealing tip connection member 50 may be trimmed at or below the skin surface of the patient upon removal of the vascular closure device 10 from the patient.

The detachable sealing tip 48 may have an outer profile that is no greater than an outer profile of the carrier tube 44 of the balloon location device 14, or no greater than an outer profile of any portion of the balloon location device 14 that is distal of the housing 42. For example, a maximum dimension $D_4$ of the detachable sealing tip 48 may be no greater than a maximum dimension $D_3$ of the carrier tube 44 as shown in FIG. 9B. The detachable sealing tip 48 may be detachable from the balloon location device 14 without the use of a friction or interference fit between the detachable sealing tip 48 and the channel of the sealant within which the detachable sealing tip 48 is deposited.

Referring now to FIGS. 4-8, the vascular closure device 10 is shown sealing a vessel puncture 92 in a vessel 90. The vessel puncture 92 is accessible through a tissue puncture 98 (also referred to as a percutaneous incision) in a tissue layer 96.

Figure 5:
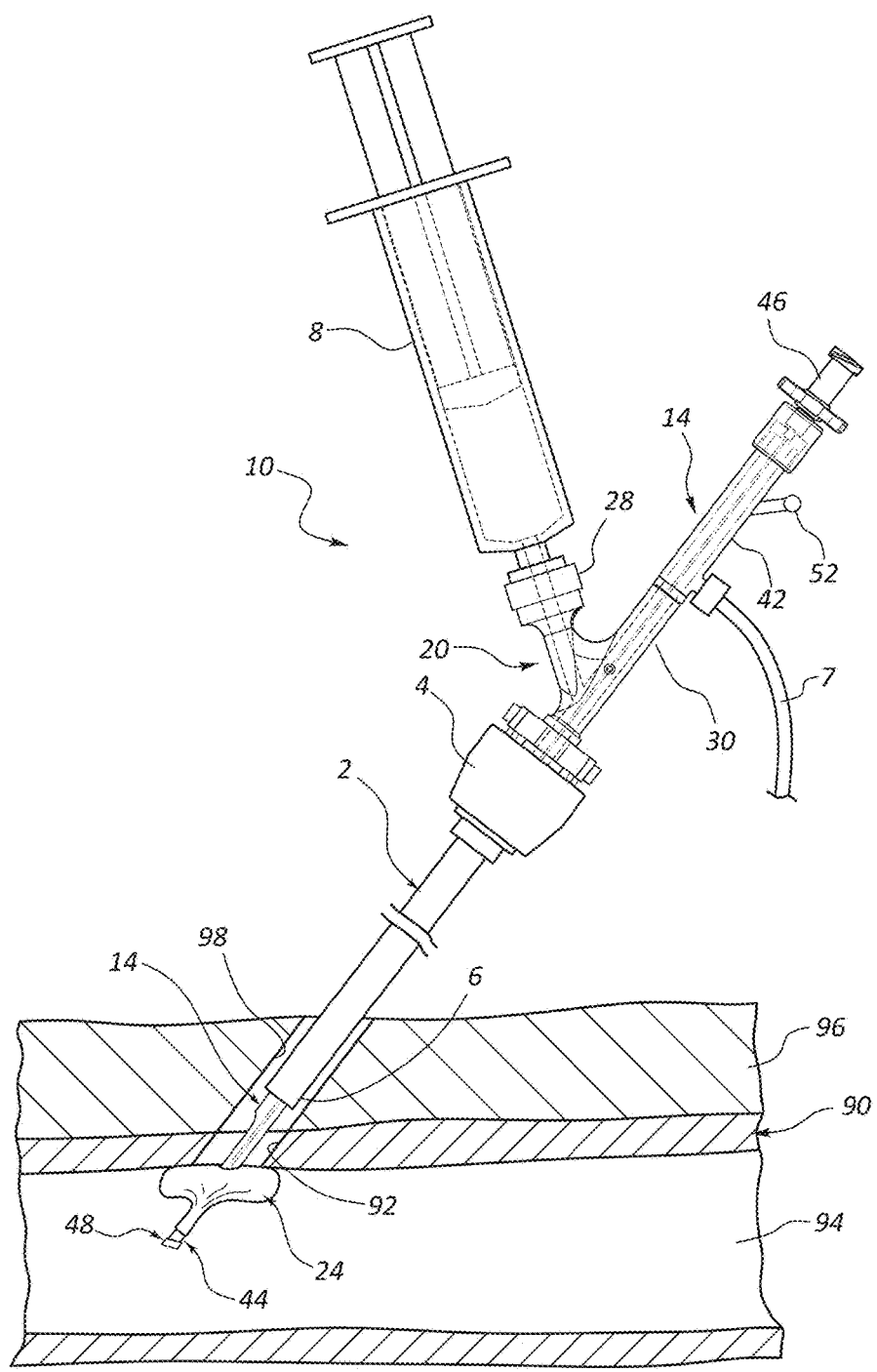

A delivery or insertion sheath 2 is advanced through the tissue puncture 98 and through the vessel puncture 92 into a vessel lumen 94 of the vessel 90 as shown in FIG. 4. The vascular closure device 10 is aligned with an opening through a hub 4 of the delivery sheath 2. FIG. 5 shows the vascular closure device 10 inserted through the delivery sheath 2 until the balloon 24 and detachable sealing tip 48 are positioned distal of a distal end 6 of the delivery sheath 2. The connector 30 of sealant delivery device 12 may connect to the hub 4 of the delivery sheath 2 so that the delivery sheath 2 and vascular closure device 10 move in tandem.

A volume of inflation fluid is delivered from a source of inflation fluid 7 and through the vascular closure device 10 to fill the balloon 24. The vascular closure device 10 and delivery sheath 2 are withdrawn proximally to contact the inflated balloon 24 against an inner surface of the vessel 90 adjacent to the vessel puncture 92. The balloon 24 may provide temporary sealing of the vessel puncture 92 (e.g., temporary hemostasis).

Figure 6:
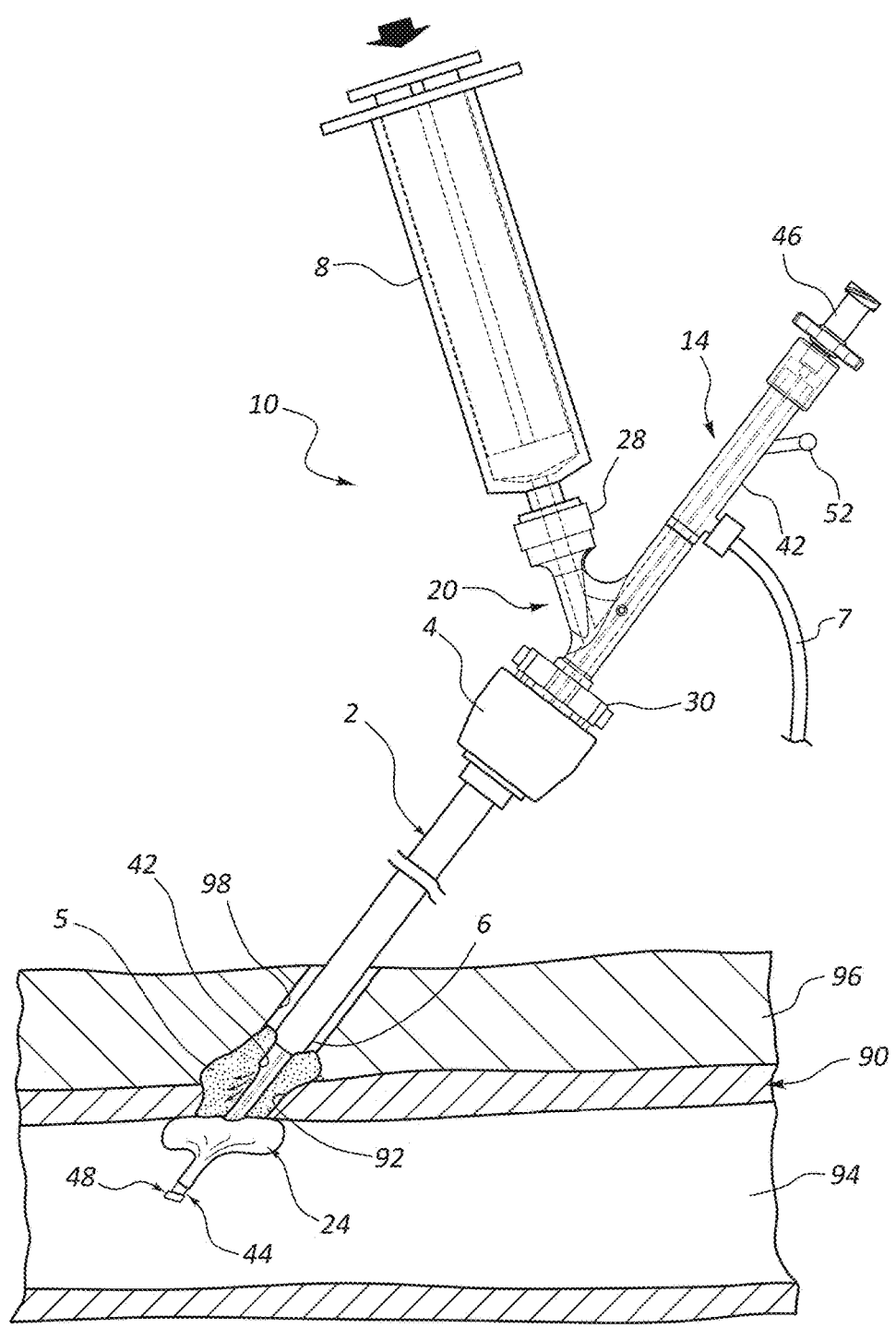

Referring to FIG. 6, a volume of sealant is delivered via a sealant source 8 through the sealant delivery device 12 and ejected through the distal opening 36 of the first lumen 32 at a location adjacent to the vessel puncture 92. The sealant forms a sealant plug 5 that fills the vessel puncture 92 and at least a portion of the tissue puncture 98. Typically, the sealant is allowed to cure to form a solid or semi-solid plug structure before deflating the balloon 24. Allowing the sealant to form into sealant plug 5 limits the risk of the sealant moving into the vessel lumen 94 after deflating the balloon 24.

Figure 7:
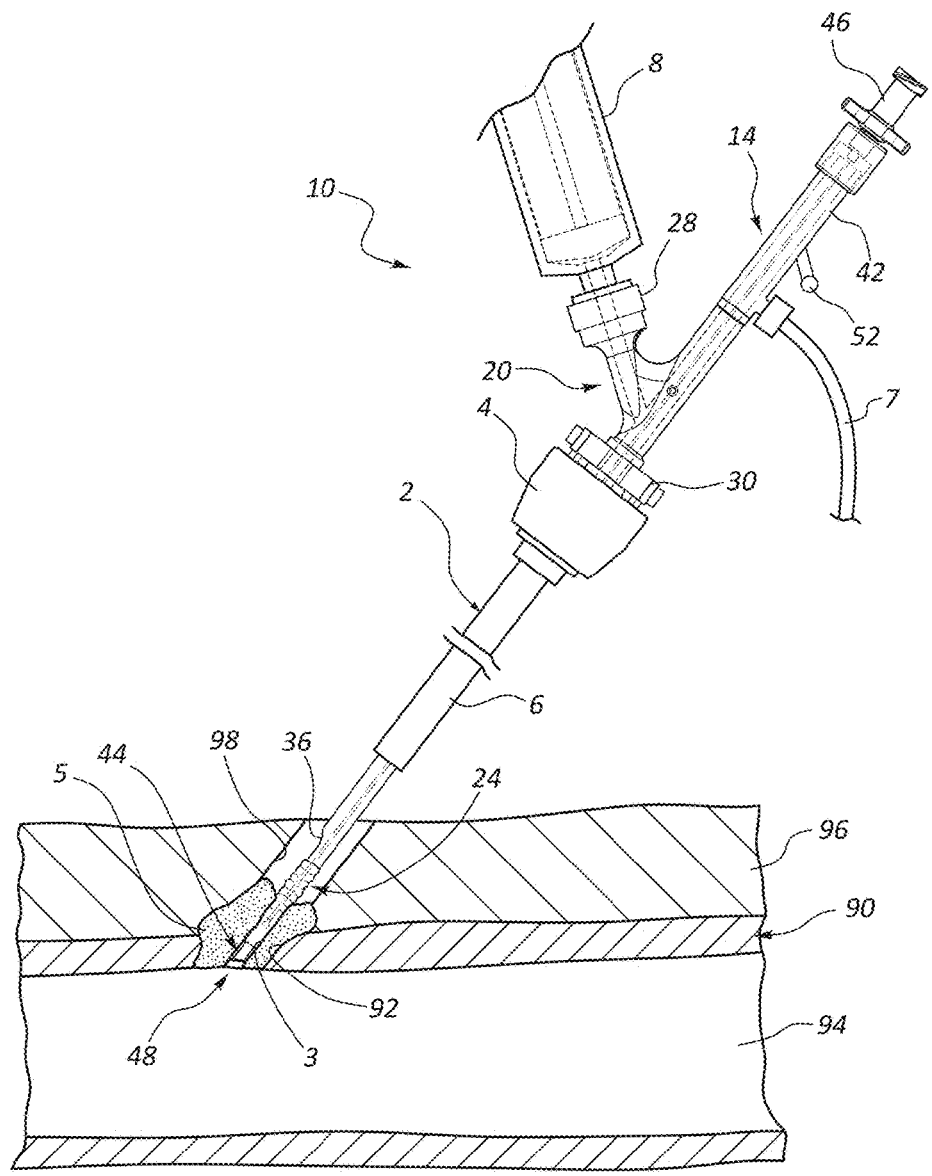

FIG. 7 shows the balloon 24 deflated and the vascular closure device 10 withdrawn through the sealant plug 5. Removal of the vascular closure device 10 forms a channel 3 through the sealant plug 5. The vascular closure device 10 is withdrawn to a position in which the detachable sealing tip 48 is positioned within the channel 3. The operator then operates the actuator 52 to release the detachable sealing tip 48 to seal the channel 3. As discussed above, the detachable sealing tip 48 may be released by disconnecting the sealing tip connection member 50 from the detachable sealing tip 48.

The angled shape of the face 75 may align with an interior or exterior surface of the vessel 90. The angled shape of the face 75 may provide a flush mount arrangement of the detachable sealing tip 48 with the interior or exterior surface of the vessel 90 and may help maintain the detachable sealing tip 48 outside of the vessel lumen 94 as shown in FIG. 8.

Figure 8:
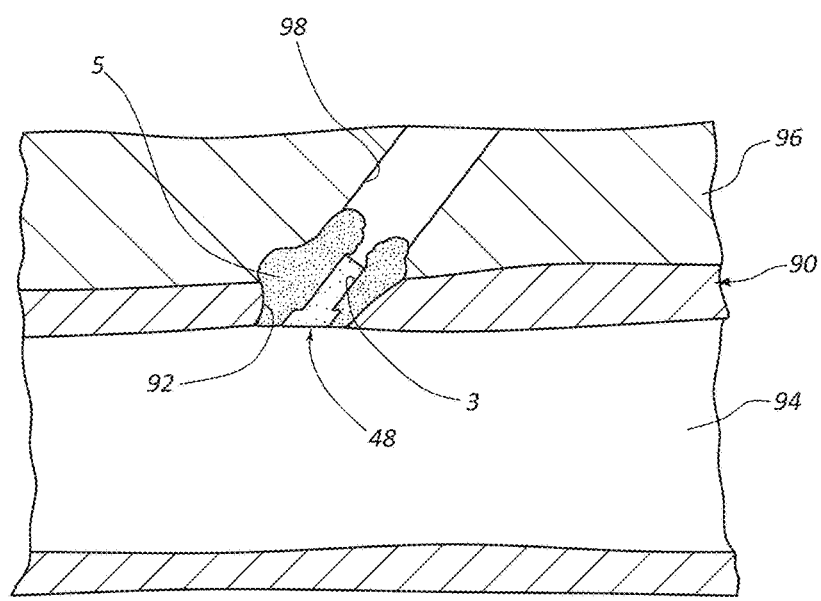

After detaching the detachable sealing tip 48, the vascular closure device 10 may be completely removed from the patient to leave behind the sealant plug 5 with the channel 3 at least partially filled by the detachable sealing tip 48 (see FIG. 8).

The detachable sealing tip 48 may be positioned at any location along the length of the channel 3. The detachable sealing tip 48 may be positioned spaced apart from the vessel lumen 94 and may be positioned outside of the vessel wall such as adjacent to an exterior wall of the vessel 90.

Figure 12:
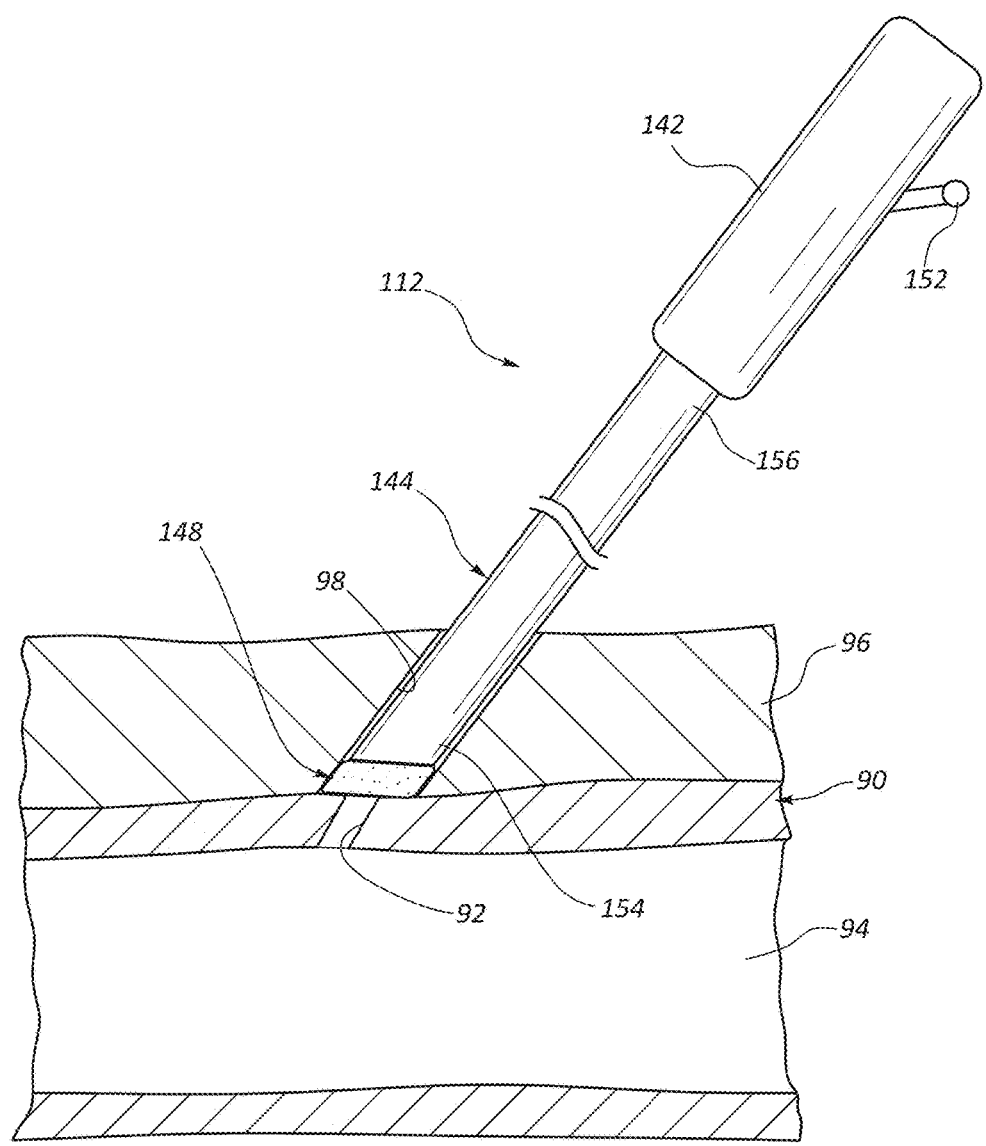
FIGS. 12-14 show another example vascular closure device in use sealing a vessel puncture in accordance with the present disclosure.
Figure 13:
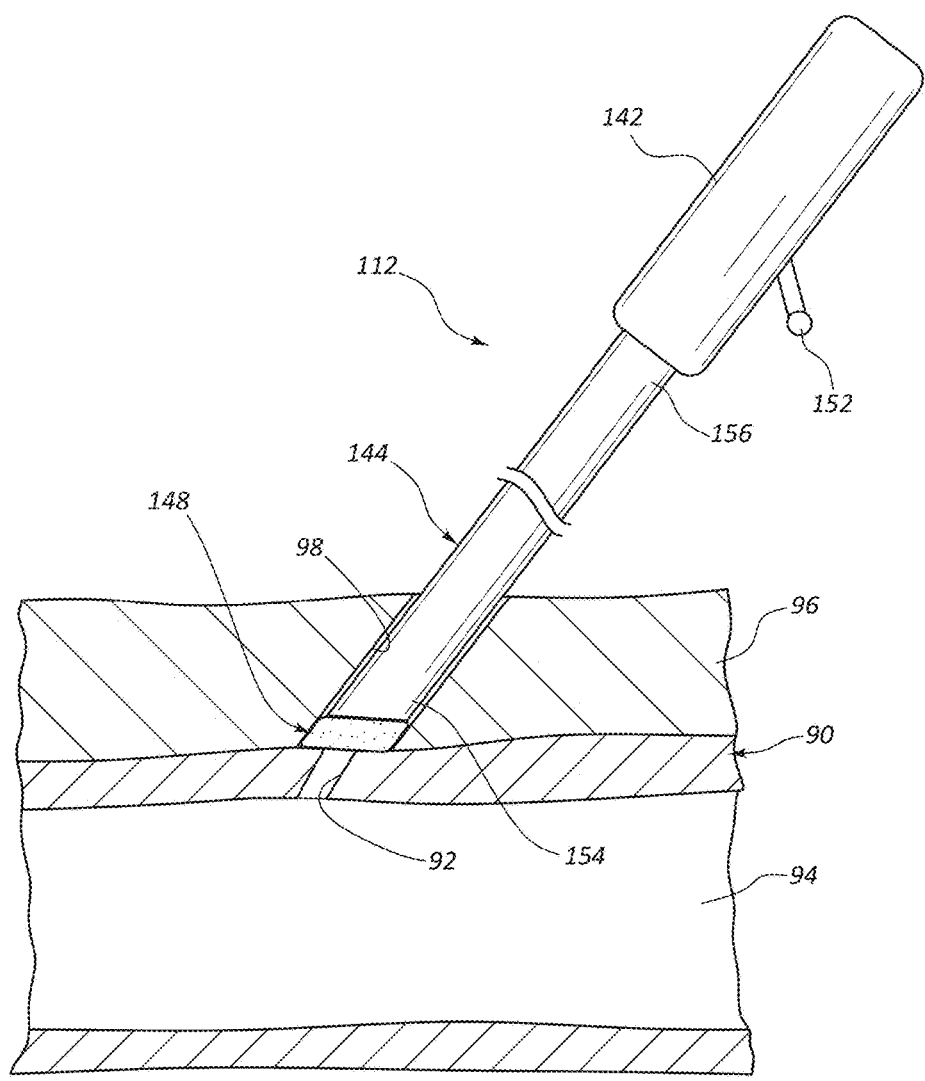
Figure 14:
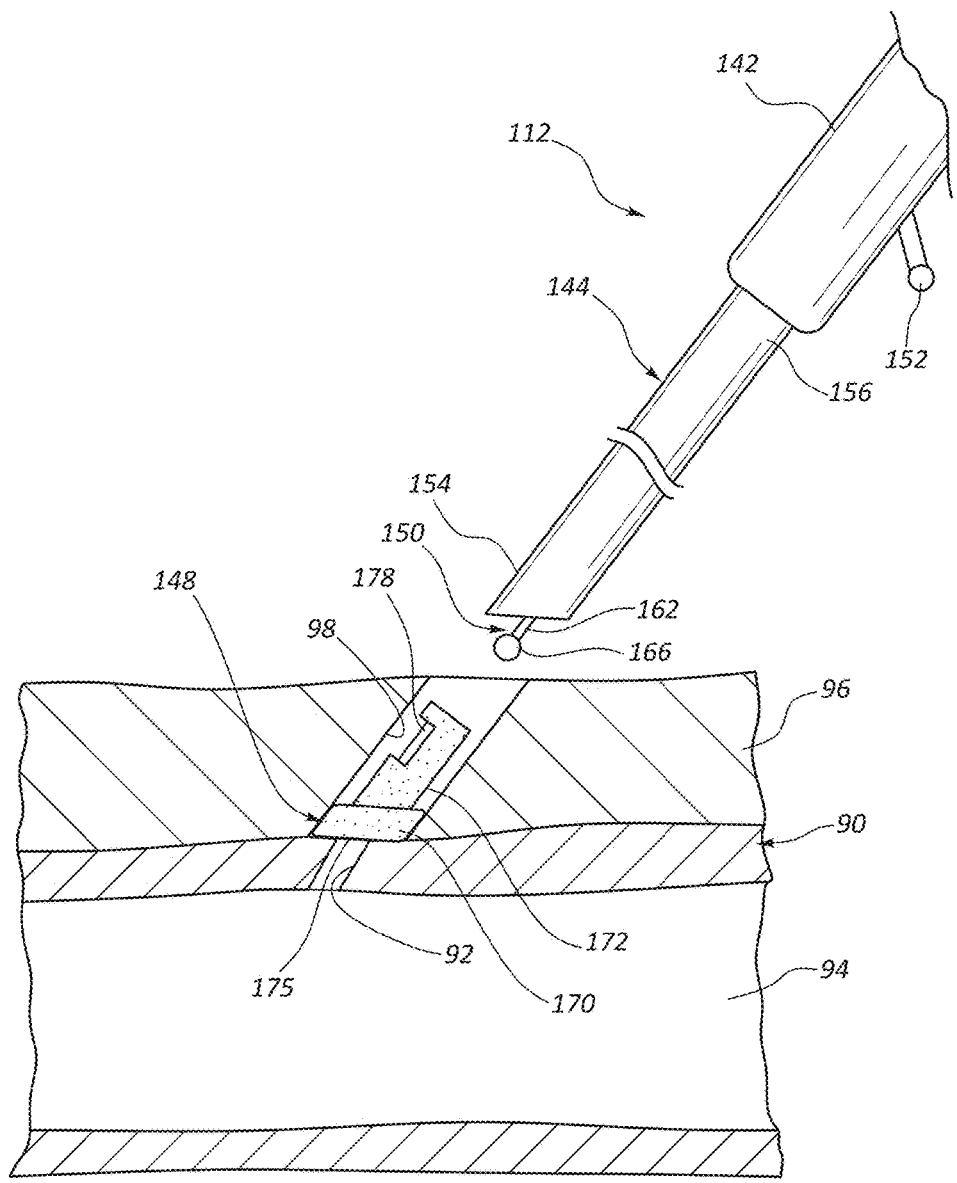

Referring now to FIGS. 12-14, another example device using a detachable sealing tip is shown and described. The device may include a sealant delivery device 112 that includes a housing or handle 142, a carrier tube 144 having distal and proximal ends 154, 156, a detachable sealing tip 148, and an actuator 152. The detachable sealing tip 148 may include a head portion 170 and a body portion 172 (see FIG. 14). The body portion 172 may include a side opening 178 through which a sealing tip connection member 150 having a connection portion 166 at its distal end 162 is inserted to provide a temporary connection of the detachable sealing tip 148 to the sealant delivery device 112.

The sealing tip connection member 150 may be coupled to the actuator 152. Operating the actuator 152 may release the sealing tip connection member 150 from the detachable sealing tip 148 to deposit the detachable sealing tip 148 adjacent to a vessel puncture 92.

The sealant delivery device 112 may be operable to deposit the detachable sealing tip 148 without a balloon location device or other locating device that is inserted into the vessel. The sealant delivery device 112 may be used with or without a delivery sheath 2 (e.g. see device of FIGS. 4-8). FIGS. 12-14 show use of the sealant delivery device 112 without a delivery sheath and without a balloon location device or other locating device.

Referring to FIG. 12, the sealant delivery device 112 is inserted through a tissue puncture 98 to position the detachable sealing tip 148 adjacent to a vessel puncture 92. The actuator 152 is operated to release the sealing tip connection member 150 from the detachable sealing tip 148 to deposit the detachable sealing tip 148 adjacent to the vessel puncture 92 as shown in FIG. 13. The sealant delivery device 112 is then withdrawn from the tissue puncture 98, thereby leaving behind the detachable sealing tip 148 as shown in FIG. 14. The detachable sealing tip 148 seals the vessel puncture 92.

In other arrangements, the detachable sealing tip 148 is at least partially positioned within the vessel puncture 92 as opposed to being positioned entirely out of the vessel puncture as shown in FIG. 14. The detachable sealing tip 148 may have any desired shape and size. In at least one example, a maximum outer dimension of the detachable sealing tip 148 is no greater than a maximum outer dimension of the carrier tube 144 as shown in FIGS. 12-14. Other arrangements may provide the detachable sealing tip 148 having a maximum outer dimension that is less than the maximum outer dimension of the carrier tube 144, thereby limiting inadvertent catching or snagging of the detachable sealing tip 148 with features in and around the vessel puncture 92 that would inhibit proper placement of the detachable sealing tip 148 directly adjacent to or within the vessel puncture 92.

The detachable sealing tip 148 is shown having a distal surface that is arranged at a non-perpendicular angle relative to a longitudinal axis of the detachable sealing tip 148. The angle of the distal surface 175 may substantially match an insertion angle of the sealant delivery device 112 through the tissue puncture 98 so that the distal surface 175 rests flush against an exterior surface of the vessel 90 (see FIG. 14).

In addition to the various embodiments described above with reference to FIGS. 1-14, several methods may be possible using the disclosed systems and devices. One method may relate to a method of sealing a tissue puncture such as an arterial puncture. Other methods may be directed to assembling a vascular closure device in a way that provides a releasable connection of a detaching sealing tip to the vascular closure device. Release of the detachable sealing tip may be performed by operating an actuator at a handle portion of the vascular closure device at a proximal end portion thereof. The detachable sealing tip may be released by applying a proximally directed tension force in a sealing tip connection member (e.g., an elongate wire, suture or filament). The sealing tip connection member may be connected to the sealing tip with a releasable connection such as a press-fit, snap-fit or interference fit connection.

While this invention has been described with reference to certain specific embodiments and examples, it will be recognized by those skilled in the art that many variations are possible without departing from the scope and spirit of this invention. The invention, as defined by the claims, is intended to cover all changes and modifications of the invention which do not depart from the spirit of the invention.

What is claimed is:

1. A vascular closure device, comprising:
    a handle;
    a carrier tube extending from the handle, the carrier tube having a distal end;
    a sealing tip positioned at the distal end of the carrier tube, the sealing tip being configured to be released adjacent to a vessel of a patient, the sealing tip comprising:
        a head portion having a longitudinal axis, a distally-facing end surface, and a single planar stop surface, the distally-facing end surface being oriented at a non-perpendicular angle relative to the longitudinal axis, the single planar stop surface being oriented at the non- perpendicular angle relative to the longitudinal axis, the distally-facing end surface being configured to rest flush against an outer surface of the vessel, the single planar stop surface being configured to abut the distal end of the carrier tube,
        a body portion extending proximally from the single planar stop surface along the longitudinal axis, the body portion being configured to be positioned inside the carrier tube while the head portion is positioned outside the distal end of the carrier tube, the head portion and body portion being integrally formed as a single piece, the sealing tip including the head portion and the body portion being detachable in its entirety from the closure device, and
        a cavity extending through the sealing tip, the cavity having a first opening and a second opening, the first opening being positioned in a laterally-facing surface of the body portion, the second opening being positioned in a proximally-facing end surface of the sealing tip, the first and second openings being positioned proximal to the single planar stop surface;

a sealing tip connection member extending from the sealing tip to the handle, the sealing tip connection member having a distal end extending into the cavity through the second opening and removable through the second opening;

an actuator mounted to the handle and operable to move the sealing tip connection member to release the sealing tip from the carrier tube.

2. A vascular closure device according to claim 1, wherein the sealing tip connection member comprises a wire having a retention member at a distal end thereof, and applying a tension force in the wire with the actuator disconnects the retention member from the sealing tip.

3. A vascular closure device according to claim 1, wherein the carrier tube includes a lumen, and the sealing tip connection member extends through the lumen.

4. A vascular closure device according to claim 3, further comprising a hypotube extending through the lumen, and the sealing tip connection member extends through the hypotube.

5. A vascular closure device according to claim 1, wherein the cavity is sized to receive a connection portion of the sealing tip connection member, the connection portion being releasable from the cavity upon operation of the actuator.

6. A vascular closure device according to claim 5, wherein the first opening is in a sidewall of the sealing tip, the sealing tip connection member being insertable through the first opening and out of the second opening with the connection portion being retained in the cavity.

7. A vascular closure device for sealing a vessel puncture of a patient, comprising:

a sealant delivery device configured to deposit a volume of flowable sealant adjacent to a vessel puncture in a vessel;

a detachable sealing tip assembly configured to seal a channel formed in the volume of flowable sealant upon removal of the vascular closure device from the patient, the detachable sealing tip assembly comprising:

a carrier tube having a distal end;

a sealing tip positioned at the distal end of the carrier tube, the sealing tip comprising a head portion, a body portion, and a planar stop surface, the head portion being integrally formed with the body portion as a single piece with the planar stop surface positioned between the head and body portions, the body portion being configured to be positioned inside the carrier tube while the head portion is positioned outside the distal end of the carrier tube and the planar stop surface abuts the distal end of the carrier tube, the sealing tip being detachable in its entirety from the closure device, wherein the head portion and the body portion are both detachable from the closure device, the head portion having a distally-facing end surface, the distally-facing end surface being oriented at a non-perpendicular angle relative to a longitudinal axis of the sealing tip, the planar stop surface being oriented at the non-perpendicular angle relative to the longitudinal axis of the sealing tip, the distally-facing end surface being configured to rest flush against an outer surface of the vessel;

a cavity formed in the sealing tip, the cavity having a first opening and a second opening, the first and second openings being positioned proximal to the planar stop surface, the first opening being positioned in a laterally-facing surface of the body portion, the second opening being positioned in a proximally-facing end surface of the sealing tip;

a filament having a distal end releasably connected to the sealing tip within the cavity through the second opening and a proximal end operable by an actuator to disconnect the sealing tip from the distal end of the filament within the channel.

8. A vascular closure device according to claim 7, wherein the sealant delivery device comprises a lumen sized to receive the carrier tube.

9. A vascular closure device according to claim 7, wherein the filament is connected to the sealing tip prior to inserting the sealing tip into the carrier tube.

10. A vascular closure device according to claim 7, wherein the filament comprises one of a wire and a suture.

11. A method of sealing a vessel puncture in a vessel of a patient, comprising:

providing a vascular closure device having a carrier tube, a sealing tip, a sealing tip connection member, and an actuator, the sealing tip connection member extending from the sealing tip to the actuator, the carrier tube comprising a distal end with a distal end surface, the sealing tip comprising a head portion and a body portion, the sealing tip comprising a planar stop surface between the head portion and the body portion, the body portion being configured to be positioned inside the carrier tube while the head portion is positioned outside the distal end of the carrier tube and the planar stop surface abuts the distal end surface of the carrier tube, the sealing tip including the head portion and the body portion being detachable in its entirety from the closure device, the head portion having a distally-facing end surface oriented at a non-perpendicular angle relative to a longitudinal axis of the sealing tip, the planar stop surface being oriented at the non-perpendicular angle relative to the longitudinal axis of the sealing tip;

advancing the vascular closure device to the vessel puncture;

delivering a volume of flowable sealant to the vessel puncture;

withdrawing a portion of the vascular closure device through the volume of flowable sealant to define a channel in the volume of flowable sealant;

positioning the sealing tip in the channel with the distally-facing end surface of the sealing tip being flush against an outer surface of the vessel and with the sealing tip connection member positioned within a cavity in the sealing tip, the cavity having a first opening and a second opening positioned proximal to the planar stop surface, the first opening being positioned in a laterally-facing side wall of the body portion, the second opening being positioned in a proximally-facing end wall of the sealing tip, a distal end of the sealing tip connection member extending through the second opening;

operating the actuator to release the sealing tip connection member from the sealing tip to seal the channel by withdrawing the distal end of the sealing tip connection member through the second opening of the cavity.

12. A method according to claim 11, wherein operating the actuator to release the sealing tip connection member from the sealing tip includes removing a connection portion of the sealing tip connection member from within the sealing tip.

13. A method according to claim 11, wherein the sealing tip is releasably connected to the distal end of the carrier tube, wherein releasing the sealing tip connection member from the sealing tip disconnects the sealing tip from the carrier tube.

14. A method according to claim 11, wherein operating the actuator applies tension in the sealing tip connection member.

15. A method according to claim 11, further comprising providing a sealant delivery device to deliver the volume of flowable sealant to the vessel puncture, the vascular closure device extending through the sealant delivery device.

16. A method of assembling a vascular closure device, comprising:
  providing a sealing tip, a sealing tip connection member, an actuator, a handle, a carrier tube, and a sealant delivery device, the sealing tip having a cavity with first and second access openings, the sealing tip connection member having a connection portion at a distal end thereof, and the actuator being mounted to the handle, the carrier tube comprising a distal end surface, the sealing tip comprising a head portion and a body portion, the sealing tip having a distally-facing end surface and a planar stop surface, the planar stop surface positioned between the head portion and the body portion, the distally-facing end surface being oriented at a non-perpendicular angle relative to a longitudinal axis of the sealing tip, the planar stop surface being oriented at the non-perpendicular angle relative to the longitudinal axis of the sealing tip, the first and second access openings being positioned proximal to the planar stop surface, the first access opening being positioned in a laterally-facing surface of the body portion, the second access opening being positioned in a proximally-facing end surface of the sealing tip, the body portion being configured to be positioned inside the carrier tube while the head portion is positioned outside the distal end of the carrier tube and the planar stop surface abuts the distal end surface of the carrier tube, the sealing tip including the head portion and the body portion being detachable in its entirety from the closure device;
  inserting a proximal end portion of the sealing tip connection member into the cavity of the sealing tip through the first access opening and out of the cavity through the second access opening, the connection portion being releasably held in the cavity;
  inserting the body portion of the sealing tip into a distal open end of the carrier tube, wherein the planar stop surface of the head portion of the sealing tip contacts the distal end surface of the carrier tube;
  connecting the proximal end portion of the sealing tip connection member to the actuator;
  wherein the sealant delivery device is operable to deliver a volume of flowable sealant to a vessel puncture with the distally-facing end surface of the sealing tip positioned flush against an outer surface of a body vessel, and the actuator being operable to disconnect the sealing tip connection member from the sealing tip to deposit the sealing tip within the volume of flowable sealant.

17. A method according to claim 16, wherein the connection portion has a minimum size that is greater than a maximum size of the second access opening.

* * * * *